United States Patent [19]

Finlan

[11] Patent Number: 4,767,719
[45] Date of Patent: Aug. 30, 1988

[54] ASSAY APPARATUS HAVING PIEZOELECTRIC SLAB GENERATING EFFECTIVE DIFFRACTION GRATING IN APPLIED ANALYTE-SPECIFIC FILM

[75] Inventor: Martin F. Finlan, Little Chalfont, England

[73] Assignee: Amersham International plc, Little Chalfont, England

[21] Appl. No.: 51,582

[22] Filed: May 20, 1987

[30] Foreign Application Priority Data

May 20, 1986 [GB] United Kingdom ............... 8612221

[51] Int. Cl.[4] .................. G01N 21/17; G01N 33/53
[52] U.S. Cl. .................................. 436/501; 324/71.5;
350/162.11; 356/364; 422/68; 436/518;
436/528; 436/805; 436/806; 436/807
[58] Field of Search ............... 356/364; 324/71.5;
350/162.11; 436/518, 528, 805, 806, 807;
422/68

[56] References Cited

U.S. PATENT DOCUMENTS

| 4,236,893 | 12/1980 | Rice | 436/531 X |
|---|---|---|---|
| 4,242,096 | 12/1980 | Oliveira | 436/513 X |
| 4,314,821 | 2/1982 | Rice | 436/806 X |
| 4,498,045 | 2/1985 | Dworsky | 324/71.5 |
| 4,508,832 | 4/1985 | Carter | 356/364 X |
| 4,521,522 | 6/1985 | Lundstrom | 356/364 X |
| 4,523,847 | 6/1985 | Bjorklund | 356/364 X |
| 4,537,861 | 8/1985 | Elings | 436/805 X |
| 4,565,983 | 1/1986 | Gratze | 350/162.11 X |
| 4,647,544 | 3/1987 | Nicoli | 436/805 X |
| 4,704,353 | 11/1987 | Humphries | 436/806 X |

FOREIGN PATENT DOCUMENTS

WO84/02578  7/1984  PCT Int'l Appl. .

Primary Examiner—Sidney Marantz
Attorney, Agent, or Firm—Wenderoth, Lind & Ponack

[57] ABSTRACT

A method and apparatus for assaying a species in a biological sample fluid. The apparatus comprises an SAW device (1) comprising a slab (2) of piezoelectric material on the upper surface (5) of which is formed an input transducer (3) and an output transducer (4). A source of RF energy is applied to the input transducer to generate a surface acoustic wave. Applied to the surface (5) is a thin layer (8) of a material capable of binding a species to be assayed. The sample (13) to be tested is applied to the top of the layer (8). A collimated light beam (1) from a source (9) is applied to the thin film from underneath the slab (2) and is collected by a photodetector (12). When the slab (2) is energized, the vibration sets up an effective diffraction grating which is coupled to the thin film and acts to diffract the light beam (10) applied to it. The energy in the diffracted beam, as measured by the photodetector (12), is indicative of the progress and result of the reaction between the layer 8 and the sample.

14 Claims, 1 Drawing Sheet

ASSAY APPARATUS HAVING PIEZOELECTRIC SLAB GENERATING EFFECTIVE DIFFRACTION GRATING IN APPLIED ANALYTE-SPECIFIC FILM

This invention relates to a method of assaying a species in a liquid sample, generally a biological fluid, and to apparatus for use with such method.

It is known from international patent application WO84/02578 that the properties of a sample may be detected by applying to an optically active part of the surface of a substrate a thin film of a material capable of binding a species to be assayed and thence applying the sample onto the thin film and observing the change in the optical properties of the surface as the species within the sample bonds to the applied thin film. In the preferred embodiment of the invention, this "optically active" surface is a grating. A beam of suitably polarised light incident on the grating will give rise to diffraction or reflection properties which are dictated by the manner in which the sample reacts with the applied thin film of material. The angle of incidence of the beam may be a right angle, or may be variable, resulting in a reflectivity dip at a particular angle.

The present invention seeks to improve on the sensitivity and versatility of this technique by providing that the aforsaid thin film of material is applied to the surface of a slab of piezoelectric material which latter is thence energising by means of electrical energy applied to a suitable electrode or electrodes. Vibrations within the piezoelectric material are coupled into the thin film which then exhibits the properties of a grating. Polarised light incident on the coated surface of the piezoelectric material can be detected after diffraction using a photodetector or simlar, or alternatively the energy in the form of a plasmon wave, coupled into the piezoelectric material at the aforementioned dip at particular angles of incidence, may be detected.

The invention also provides an apparatus for use with such method.

Piezoelectric mateirals may be excited in such a way as to produce primarily surface waves or primarily bulk waves. The waves may travel continuously through the material or may form a stationary standing wave pattern. It is believed that the use of surface-wave excitation will be of particular application in the present invention. Devices which use such excitation, known as surface acoustic wave (SAW) devices, comprise one or more transducers formed on the surface of a slab of a suitable piezoelectric material. An ac signal applied to one of the transducers causes an acoustic wave to be launched from that transducer which wave propagates along the surface of the piezoelectric material to a distant transducer or transducers where it may be reconverted into an ac signal. The properties of the SAW device determine the frequency of the waves which can propagate along the surface and the device thus acts electrically as an effective bandpass filter. The slight delay which occurs as the wave travels from one transducer to the other can be utilised in applications requiring a delay line.

The wave, whether travelling or standing, produces alternate areas of compression and rarefaction of the atoms of the material. In a surface-wave device, as distinct from a bulk-wave device, the wave propagates more slowly because the atoms at the surface are less firmly anchored than those within the material.

Suitable piezoelectric materials include lithium niobate and polyvinvylidene fluoride. The former of these has a number of attractive properties which make it particularly suitable in this application. It is a stand-along substrate, is resistant to water an dmost acids, is optically transparent within the wavelength range 450 to 5000 nm, has a high melting point (1260° C.) and Curie temperature (1210° C.), a refractive index greater than 2.15 and is mechanically robust. Being a common component of SAW devices, it is available in quantity in single crystal form and there is considerable expertise available in the deposition of electrodes onto it and the modification of its structure by diffused metals.

Polyvinylidene fluoride is a piezoelectric polymer, is stable in aqueous environments up to 120° C. with a broad band response (up to 10 GHz), but with an acoustic impedance only 2–3 times that of water. This latter is a disadvantage compared with ceramic or lithium niobate, whose acoustic impedance is about 16 times that of water, where decoupling from serum or other aqueous solutions is required.

Other piezoelectirc materials may have an advantage if the device is to be fabricated by deposition on a substrate, for example by sputtering, CVD processes etc. These could be zinc oxide or tantalum pentoxide, for example.

The radiation incident on the surface of the piezoelectric material is electromagnetic radiation and is preferably in the visible region. The radiation interacts at the surface of the piezoelectric material so as to be diffracted and the diffracted light may be detected by a photodetector such as a strip imager, photodiode or charge-coupled device (CCD). Since the transparancy of the sample (e.g. serum) is likely to be less than that of the piezoelectric material it may well be preferable to project the light from beneath (i.e. through the piezoelectric material), rather than from above and through the sample. The absorption of the light in diffusing through the device is a function of the properties of the coating applied to the surface of the piezoelectric material and is thus representative of the status of the reaction between the film and a sample applied thereto. The maximum absorption dip occurs at particular angles of incidence and this in itself is dictated by the coating properties. Thus the properties of the coating can be studied either by keeping the angle of incidence steady, and observing the change in absorption which occurs as the reaction between the applied film and the sample takes place, or by "tuning" the angle of incidence for a dip as the reaction progresses or both. Such tuning can be carried out automatically using feedback techniques. Tuning can also be effected by varying the frequency of the excitation signal applied to the piezoelectric material. For example, one possible method using an SAW device is to tune for dip before the sample is added, then tune the SAW drive frequency to follow the dip as the reaction progresses. As before this can be achieved automatically using feedback techniques.

The tuning for a dip is likely to be the most sensitive method. It is now known that the dip results form the coupling into the material of the grating—in this case the thin film of material coating the surface of the piezoelectric material—of energy which travels close to the surface of the material in the form of a surface plasmon polarition. The plasmon wave is associated with an evanescent wave which travels with the plasmon wave above the surface and indeed maintains the plasmon wave. The energy in the plasmon wave can be extracted from the material at a discontinuity, such as an edge, or further diffraction grating, and can be detected using suitable detectors. Thus it will be seen that there are two ways of detecting the dip:
(1) Look for the minimum diffracted energy;
(2) Look for the maximum absorbed energy, as represented by the energy extracted at a discontinuity from the plasmon wave.

In order that the invention may be better understood, several embodiments thereof will now be described by way of example only and with reference to the accompanying drawings in which.

Figure 1:
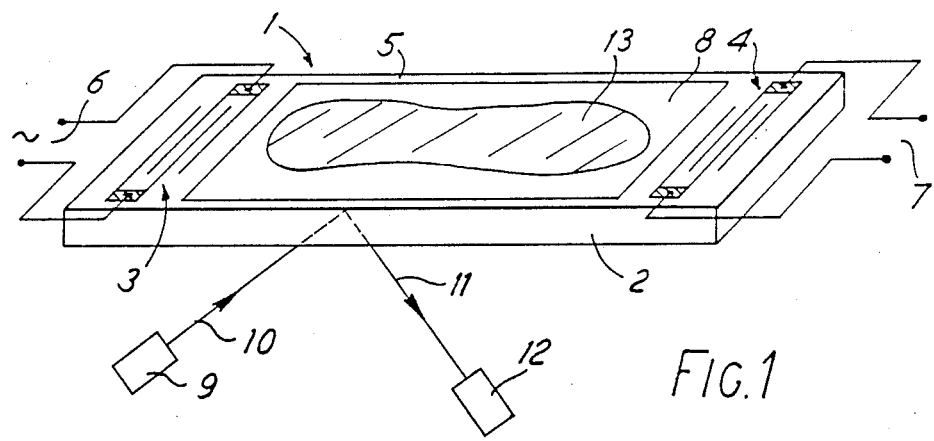
FIG. 1 is a diagrammatic perspective view of an apparatus for use in the method of the invention.
Figure 2:
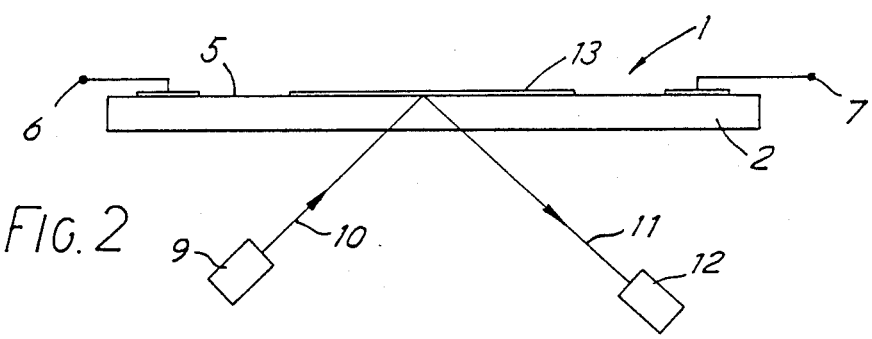
FIG. 2 is a side elevation of the apparatus of FIG. 1.

Referring to FIGS. 1 and 2, the apparatus comprises an SAW device 1 comprising a slab 2 of piezoelectric material such as a crystal of lithium niobate. An input transducer 3 and an output transducer 4 are formed on the top surface 5 of the slab 2. Each transducer is formed from two sets of interleaved fingrs of metallisation on the surface 5 and respective connections from the two sets of fingers are brought out to form input terminals 6 and output terminals 7. A source, not shown, of RF energy is applied to the input terminals 6 and may be picked up at the output terminals 7 by a suitable detector (also not shown). Since this invention does not rely on the monitoring of the output terminals, these, and the output transducer itself, may in certain circumstances be omitted, and a standing wave set up with just a single transducer acting as both input and output. It is likely that this will imply a different physical arrangement to that shown in FIG. 1.

In the two transducer arrangement shown an RF signal applied to the input terminals generates at the input transducer a surface acoustic wave which travels across the surface creating compressions and rarefactions as the waves pass a particular point on the surface or a pattern of stationary compressions and rarefractions if a standing wave is set up. The attenuation of the wave in passing across the surface can be measured at the output terminals and indeed this measurement can itself act as a means for analysing the sample since the attenuation is dependent upon the nature of the surface and in particular the characteristics of any reaction which takes place on it.

Applied to the surface 5 is a thin layer 8 of uniform thickness and made of a material capable of binding the species to be assayed. If necessary a thin interlayer (not shown), for example of sputter-deposited gold, may be formed between the layer 8 and surface 5 in order to ensure the adhesion of the layer 8 to the surface. The material of the layer 8 and the species should form a specific binding pair, the nature of which is not critical. When the species is an antigen or a hapten, the material is preferably its associated antibody. The sample may conveniently be of a biological fluid, such as serum or plasma.

A light source 9 generates a collimated beam 10 of suitable polarised light which is incident on the surface 5 from beneath the slab 2. Zero order diffracted light 11 is collected by a photodetector 12 which may take several forms, depending upon the circumstances: examples include a photo diode or photo-diode array, charge-coupled devices, a strip imager or a dynamic RAM imaging chip. The order of the light collected has no particular significance except that, having made the choice, consistency should be maintained.

As shown the light is incident from beneath the slab, this being to avoid possible attenuation in the sample; however there is no reason why light sould not be incident from above and, in some circumstances, this may be preferred. A further variation is that the incident light could be pulsed in order to provide better discrimination over ambient light.

It is known that light of appropriate polarisation is absorbed when incident onto a diffraction grating at an angle of incidence that is a function of the coating properties of the grating and that the angle at which maximum absorption takes place—the dip—changes when the coating properties change. The generation of a surface acoustic wave on the surface 5 creates a diffraction grating in the layer 8 and a measure can be taken at photodetector 12 of the amount of light diffracted by the presence of the antibody 8 alone. In order to perform a test, a sample 13 of fluid is added and an initial measure made before any reaction has commenced. After a suitable period has elapsed, a final measurement is taken and the change between the initial and final measurements noted. This information can be used to assess the nature of the change in the surface properties, and in particular the concentration of antigen within the sample, as the antibodylayer 8 changes on reaction with the analyte. It may be preferable to continuously monitor the level of light received at the photodetector during the test, rather than relying solely on discrete measurements taken at the beginning and end of the reaction. The manner in which the received light changes can give useful information.

A more sensitive measure can be achieved by searching for the null in the diffracted light level, this occurring at particular angles of incidence and/or SAW device drive frequency. To do this, the null is found immediately after addition of the sample 13, either by moving the light source 9 to alter the angle of incidence, or by altering the drive frequency. Then, after waiting a predetermined time for the reaction to take place, the null can be re-found, using the same method, and the change noted. As before the change is an indication of the nature of the reaction that has taken place. Continuous monitoring can also be achieved with this method by arranging that the light source 9 is moved or drive frequency changed automatically, under feedback control, to track the null. In the case where the angle of incidence is being altered to trace the null, it will be necessary to provide a multiple photodetector array as the photodetector 12 in order that the zero order diffracted light (which will also move) may be followed. A typical angle change from non-reacted to reacted would be in the region of one degree.

As well as searching for or tracking the null, it is useful to record the depth of the null since this can provide additional information to the operator.

Figure 3:
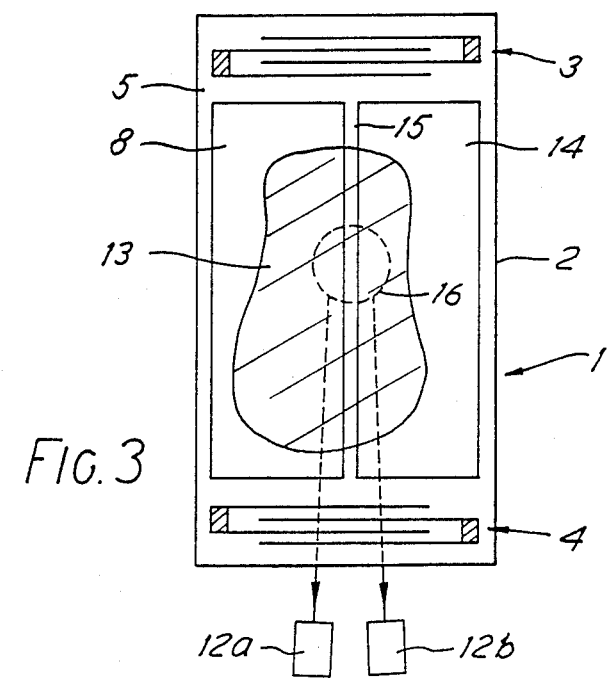
FIG. 3 is a diagrammatic plan view of an alternative embodiment.

In the practical application of this invention, some form of control should preferably be provided to eliminate temperature and other interfering effects. FIG. 3, to which reference will now be made, shows one way to achieve this.

In FIG. 3, two thin layers are laid down on the surface 5 of the piezoelectric crystal. The first of these, reference 8 as before, contains antibodies to the expected antigen within the sample. The second, referenced 14, is identical with the first except that it is a non-specific coating. A narrow dividing line 15 separates the two ares 8 and 14, and the light source 9 (not shown in FIG. 3) is incident as a spot shown dotted under reference 16 about 3 mm in diameter and straddling the two areas. Light diffracted as a result of interference in the two areas is collected by separate photodetectors 12a (for area 8) and 12b (for area 14) which may each take any of the alternative forms of the photodetector 12 of FIGS. 1 and 2. The sample 13 is applied across both areas in the manner shown so that the reaction over the area 8 can be compared to the reaction over the area 14, and any compensations made.

A similar technique to that shown in FIG. 3 can be used where a sample is to be tested for a number of different antigens. To achieve this, a number of separate areas 8 of antibody can be applied to surface 5, each being specific to a different antigen.

The spot 16 of incident light is arranged to cover at least a portion of each region, as well (preferably) as a non-specific control region, to provide for simultaneous testing of a number of antigens within a sample. One way of arranging such separate areas would be by way of a number of narrow strips arranged side by side on surface 5, each strip being an antibody specific to a particular expected antigen within the sample.

What is claimed is:

1. A method of assaying a species in a liquid sample, said method comprising applying to the surface of a slab of piezoelectric material a thin film of a material capable of binding a species to be assayed, applying the sample to be assayed onto the thin film, energising the piezoelectric material in such a way as to generate vibrations in the piezoelectric material which are coupled into the thin film to thus define an effectve diffraction grating, applying a beam of electromagnetic radiation to the thin film in such a way as to be diffracted by the grating, and detecting either the thus-diffracted radiation and/or the energy in the form of a plasmon wave coupled into the piezoelectric material.

2. A method as claimed in claim 1 wherein the piezoelectric material is energised in such a way as to produce primarily surface waves.

3. A method as claimed in either one of claims 1 or 2 wherein the slab of piezoelectric material is transparent to the electromagnetic radiation, and wherein the radiation is incident on the thin film from beneath the slab.

4. A method as claimed in any one of claim 1 to 3 wherein the angle of incidence of the electromagnetic radiation is kept steady as the reaction between the film and sample takes place, and wherein the change in the absorption of the electromagnetic radiation at the grating is observed.

5. A method as claimed in any one of claims 1 to 3 wherein the angle of incidence of the electromagnetic radiation is varied during the reaction between the sample and the film in order to follow the null or dip in a diffracted radiation.

6. A method as claimed in any one of claims 1 to 3, wherein the frequency of the incident electromagnetic radiation is varied during the reaction between the sample and the film in order to follow the null or dip in the diffracted radiation.

7. A method as claimed in either one of claims 5 or 6 wherein the timing for dip or null is carried out automatically by means of negative feedback.

8. A method as claimed in any one of claims 5, 6 or 7, wherein the dip or null is detected by observing the diffracted radiation and looking for a minimum in the diffracted energy.

9. A method as claimed in any one of claims 5, 6 or 7, wherein the dip or null is detected by observing the plasmon wave and looking for a maximum in the absorbed energy.

10. Apparatus for assaying a species in a liquid sample, said apparatus comprising a slab of piezoelectric material having applied thereto a thin film of a material capable of binding a species to the assayed, means for energising said piezoelectric material in such a way as to generate vibrations which are coupled into the thin film to thus define an effective diffraction grating, a source of electromagnetic radiation for applying to the thin film a beam of radiation, and detector means for detecting either radiation diffracted by the grating, or energy in the form of a plasmon wave coupled into the piezoelectric material when the electromagnetic radiation is incident on the thin film.

11. Apparatus as claimed in claim 10 wherein the vibration generating means comprises at least one transducer formed on the surface of the piezoelectric material in such a way as to generate surface waves in the slab of piezoelectric material, and means for applying to said transducer an AC signal.

12. Apparatus as claimed in either one of claims 10 or 11, including negative feedback means for controlling the frequency or angle of incidence of the electromagnetic radiation in such a way as to automatically time for dip or null in the diffracted radiation.

13. Apparatus as claimed in any one of claims 10 or 12, wherein said slab of piezoelectric material is coated with two separate thin films of materal, one being capable of binding an expected species in a sample to be assayed, and the other being non-specific, and wherein said radiation source is such as to cause electromagnetic radiation to be incident on both films simultaneously, and wherein said detector means comprises two separate detectors, each operable to detect radiation diffracted froma respective thin film.

14. Apparatus as claimed in claim 12, wherein the piezoelectric material is coated with a plurality of such separate thin films, each film being capable of binding a particular expected species within a sample to be assayed, and wherein a separate detector is provided for each separate thin film.

* * * * *